United States Patent
Hossainy et al.

(10) Patent No.: US 7,169,404 B2
(45) Date of Patent: Jan. 30, 2007

(54) BIOLOGICALLY ABSORBABLE COATINGS FOR IMPLANTABLE DEVICES AND METHODS FOR FABRICATING THE SAME

(75) Inventors: Syed F. A. Hossainy, Fremont, CA (US); Eugene T. Michal, San Francisco, CA (US); Yiwen Tang, San Jose, CA (US)

(73) Assignee: Advanced Cardiovasular Systems, Inc., Santa Clara, CA (US)

( * ) Notice: Subject to any disclaimer, the term of this patent is extended or adjusted under 35 U.S.C. 154(b) by 169 days.

(21) Appl. No.: 10/630,261

(22) Filed: Jul. 30, 2003

(65) Prior Publication Data

US 2005/0025799 A1    Feb. 3, 2005

(51) Int. Cl.
*A61F 2/00*    (2006.01)
*A61F 2/06*    (2006.01)

(52) U.S. Cl. ...................... 424/423; 623/1.46
(58) Field of Classification Search ............. 424/423, 424/426, 78.08; 623/1, 1.42, 1.43, 1.44, 623/1.45, 1.46; 427/2.24; 523/113
See application file for complete search history.

(56) References Cited

U.S. PATENT DOCUMENTS

| | | | | |
|---|---|---|---|---|
| 4,733,665 A | 3/1988 | Palmaz | | 128/343 |
| 4,800,882 A | 1/1989 | Gianturco | | 128/343 |
| 4,886,062 A | 12/1989 | Wiktor | | 128/343 |
| 4,977,901 A | 12/1990 | Ofstead | | 128/772 |
| 5,112,457 A | 5/1992 | Marchant | | 204/165 |
| 5,328,471 A | 7/1994 | Slepian | | 604/101 |
| 5,455,040 A | 10/1995 | Marchant | | 424/426 |
| 5,464,650 A | 11/1995 | Berg et al. | | 427/2.3 |
| 5,578,073 A | 11/1996 | Haimovich et al. | | 623/1 |
| 5,605,696 A | 2/1997 | Eury et al. | | 424/423 |
| 5,667,767 A | 9/1997 | Greff et al. | | 424/9.411 |
| 5,670,558 A | 9/1997 | Onishi et al. | | 523/112 |
| 5,700,286 A | 12/1997 | Tartaglia et al. | | 623/1 |
| 5,716,981 A | 2/1998 | Hunter et al. | | 514/449 |
| 5,824,049 A | 10/1998 | Ragheb et al. | | 623/1 |
| 5,830,178 A | 11/1998 | Jones et al. | | 604/49 |
| 5,837,313 A | 11/1998 | Ding et al. | | 427/2.21 |
| 5,851,508 A | 12/1998 | Greff et al. | | 424/9.411 |
| 5,858,746 A | 1/1999 | Hubbell et al. | | 435/177 |
| 5,865,814 A | 2/1999 | Tuch | | 604/265 |
| 5,873,904 A | 2/1999 | Ragheb et al. | | 623/1 |
| 5,971,954 A | 10/1999 | Conway et al. | | 604/96 |
| 5,980,928 A | 11/1999 | Terry | | 424/427 |
| 5,980,972 A | 11/1999 | Ding | | 427/2.24 |
| 6,005,020 A | * 12/1999 | Loomis | | 523/105 |
| 6,015,541 A | 1/2000 | Greff et al. | | 424/1.25 |
| 6,042,875 A | 3/2000 | Ding et al. | | 427/2.24 |
| 6,051,648 A | 4/2000 | Rhee et al. | | 525/54.1 |
| 6,056,993 A | 5/2000 | Leidner et al. | | 427/2.25 |
| 6,060,451 A | 5/2000 | DiMaio et al. | | 514/13 |
| 6,080,488 A | 6/2000 | Hostettler et al. | | 428/423.3 |
| 6,096,070 A | 8/2000 | Ragheb et al. | | 623/1 |
| 6,099,562 A | 8/2000 | Ding et al. | | 623/1.46 |
| 6,110,188 A | 8/2000 | Narciso, Jr. | | 606/153 |
| 6,113,629 A | 9/2000 | Ken | | 623/1.1 |
| 6,120,536 A | 9/2000 | Ding et al. | | 623/1.43 |
| 6,120,904 A | 9/2000 | Hostettler et al. | | 428/423.3 |
| 6,121,027 A | 9/2000 | Clapper et al. | | 435/180 |
| 6,129,761 A | 10/2000 | Hubbell | | 623/11 |
| 6,143,037 A | * 11/2000 | Goldstein et al. | | 424/422 |
| 6,153,252 A | 11/2000 | Hossainy et al. | | 427/2.3 |
| 6,165,212 A | 12/2000 | Dereume et al. | | 623/1.13 |
| 6,486,214 B1 | * 11/2002 | Uhrich | | 514/772.5 |
| 6,730,313 B2 | * 5/2004 | Helmus et al. | | 424/423 |
| 6,756,449 B2 | * 6/2004 | Benz et al. | | 525/326.9 |
| 6,926,919 B1 | * 8/2005 | Hossainy et al. | | 427/2.25 |
| 7,070,798 B1 | * 7/2006 | Michal et al. | | 424/423 |
| 2002/0107330 A1 | * 8/2002 | Pinchuk et al. | | 525/242 |
| 2004/0253203 A1 | * 12/2004 | Hossainy et al. | | 424/78.08 |

FOREIGN PATENT DOCUMENTS

| | | |
|---|---|---|
| EP | 0 665 023 | 8/1995 |
| EP | 0 970 711 | 1/2000 |
| EP | 1 440 698 | 7/2004 |
| WO | WO 97/16133 | * 5/1997 |
| WO | WO 00/12147 | 3/2000 |
| WO | WO 00/64506 | 11/2000 |
| WO | WO 01/01890 | 1/2001 |
| WO | WO 03/072158 | 9/2003 |
| WO | WO 2004/045549 | 6/2004 |

OTHER PUBLICATIONS

PolyActiveTM Fact Sheet, "A biodegradable polymer-based drug delivery system", pp. 1-4, www.octoplus.nl/site/website/data/00084/PolyActive.pdf.*
Invitation to Pay Additional Fees for PCT/US2004/022018, filed Jul. 8, 2004, mailed May 3, 2005, 7 pgs.
Anonymous, *Polymers vs. Pain*, www.chemheritage.org/EducationalServices/pharm/asp/polasp.htm, downloaded Apr. 19, 2005, 2 pgs.
Frost et al., *Preparation and characterization of implantable sensors with nitric oxide release coatings*, Microchemical J. 74, 2003, pp. 277-288.
Meijer et al., *Observations of the bone activity adjacent to unloaded dental implants coated with Polyactive® or HA*, J. of Oral Rehabilitation 22, 1995, pp. 167-174.
Sakkers et al., *Assessment of bioactivity for orthopedic coatings in a gap-healing model*, J. of Biomedical Materials Research, vol. 36, No. 2, Aug. 1997, pp. 265-273.
Smith, *Nitric Oxide-Releasing Polymers Containing the [N(O)NO] Group*, J. Med. Chem. 39, 1996, pp. 1148-1156.

* cited by examiner

*Primary Examiner*—Sharon Kennedy
(74) *Attorney, Agent, or Firm*—Squire, Sanders & Dempsey L.L.P.

(57) ABSTRACT

Coatings for an implantable medical device and a method of fabricating thereof are disclosed, the coatings comprising a biologically degradable, biologically erodable, and/or biologically resorbable ABA or AB block copolymer. A biologically active agent can be conjugated to the block copolymer.

19 Claims, No Drawings

BIOLOGICALLY ABSORBABLE COATINGS FOR IMPLANTABLE DEVICES AND METHODS FOR FABRICATING THE SAME

BACKGROUND OF THE INVENTION

1. Field of the Invention

This invention is directed to coatings for drug delivery devices, such as drug eluting vascular stents, and methods for producing the same.

2. Description of the State of the Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location. Examples in patent literature disclosing stents which have been applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results. One proposed method for medicating stents involves the use of a polymeric carrier coated onto the surface of a stent. A solution which includes a solvent, a polymer dissolved in the solvent, and a therapeutic substance dispersed in the blend is applied to the stent. The solvent is allowed to evaporate, leaving on the stent surface a coating of the polymer and the therapeutic substance impregnated in the polymer.

Local administration of therapeutic agents via stents has shown favorable results in reducing restenosis. However, there is a great need for better and more effective coatings for local drug delivery.

SUMMARY

A medical article comprising an implantable substrate having a coating is provided, the coating includes an ABA or an AB block copolymer, the block copolymer having moieties A and B, wherein one of the moieties produces a biological response and the other moiety provides the block copolymer with structural functionality. Examples of the biological moiety include poly(alkylene glycols), poly(ethylene oxide), poly(ethylene oxide-co-propylene oxide), poly(N-vinyl pyrrolidone), poly(acrylamide methyl propane sulfonic acid) and salts thereof, sulfonated dextran, hyaluronic acid, heparin, or copolymers thereof. Examples of the structural moiety include poly(caprolactone), poly(butylene terephthalate), poly(ester amide), or copolymers thereof. The coating can include a biologically active agent incorporated into the coating, and can include a biologically active agent conjugated to the block copolymer. Examples of the biologically active agents that can be conjugated to the ABA block copolymer include paclitaxel, antisense agents, polyarginine, rapamycin and structural derivatives or functional analogs thereof, such as EVEROLIMUS, 40-O-(3-hydroxy)propyl-rapamycin, 40-O-[2-(2-hydroxy)ethoxy]ethyl-rapamycin, and 40-O-tetrazole-rapamycin, and sources of nitrogen oxide, such as diazenium diolates.

A medical article comprising an implantable substrate having a coating is provided; the coating includes phosphoryl choline or polyaspirin.

A method for fabricating a medical article is provided. The method includes applying a coating to at least a portion of an implantable substrate, the coating including an ABA or an AB block copolymer, wherein one of the moieties in the block copolymer produces a biological response and the other moiety provides the block copolymer with structural functionality.

DETAILED DESCRIPTION

1. Terms and Definitions.

The following definitions apply:

The terms "biologically degradable," "biologically erodable," "bioabsorbable," and "bioresorbable" coatings and/or polymers are defined as coatings and/or polymers that are capable of being completely degraded and/or eroded when exposed to bodily fluids such as blood and are gradually resorbed, absorbed and/or eliminated by the body. The processes of breaking down and eventual absorption and elimination of the coating and/or polymer can be caused, for example, by hydrolysis, metabolic processes, bulk or surface erosion, and the like.

Whenever the reference is made to "biologically degradable," "biologically erodable," "bioabsorbable," and "bioresorbable" stent coatings and/or polymers forming such stent coatings, it is understood that after the process of degradation, erosion, absorption, and/or resorption has been completed, no coating will remain on the stent. Whenever the terms "degradable," "biodegradable," or "biologically degradable" are used in this application, they are intended to broadly include biologically degradable, biologically erodable, bioabsorbable, and bioresorbable coatings and/or polymers.

"Biodegradability," "bioerodability," "bioabsorbability," and "bioresorbability" are defined as inherent properties of the coating and/or polymer making the coating and/or polymer biologically degradable, biologically erodable, or biologically absorbable, and biologically resorbable.

The term "biologically beneficial" refers to a biodegradable product that brings about biological benefits to the patient as a result of the degradation and absorption of the product by the patient's body.

"Fast release" is defined as in vivo release of substantially the entire amount of the drug from the stent coating in less than 15 days, for example, within 7 to 14 days. "Slow release" is defined as in vivo release of substantially the entire amount of the drug from the stent coating in 15 days or longer, for example, within 15 to 56 days.

The terms "block copolymer" and "graft copolymer" are defined in accordance with the terminology used by the International Union of Pure and Applied Chemistry (IUPAC). "Block copolymer" refers to a copolymer containing a linear arrangement of blocks. The block is defined as a portion of a polymer molecule in which the monomeric units have at least one constitutional or configurational feature absent from the adjacent portions. "Graft copolymer" refers to a polymer composed of macromolecules with one or more species of block connected to the main chain as side chains, these side chains having constitutional or configurational features that differ from those in the main chain.

2. Embodiments of the Invention.

A coating for an implantable medical device, such as a stent, according to embodiments of the present invention, can be a multi-layer structure that can include the following four layers:

(a) a drug-polymer layer (also referred to as "reservoir" or "reservoir layer") or a polymer-free drug layer;

(b) an optional primer layer;

(c) an optional topcoat layer; and/or (d) an optional finishing coat layer.

Each layer of the stent coating can be formed on the stent by dissolving the polymer or a blend of polymers in a solvent, or a mixture of solvents, and applying the resulting polymer solution on the stent by spraying or immersing the stent in the solution. After the solution has been applied onto the stent, the coating is dried by allowing the solvent to evaporate. The process of drying can be accelerated if the drying is conducted at an elevated temperature.

To incorporate a drug into the reservoir layer, the drug can be combined with the polymer solution that is applied onto the stent as described above. Alternatively, to fabricate a polymer free drug layer, the drug can be dissolved in a suitable solvent or mixture of solvents, and the resulting drug solution can be applied on the stent by spraying or immersing the stent in the drug solution. In one embodiment, the reservoir can optionally incorporate an additional active agent or drug, for example, by having the additional drug or active agent conjugated to the polymer forming the reservoir layer.

Instead of introducing the drug as a solution, the drug can be introduced as a colloid system, such as a suspension in an appropriate solvent phase. To make the suspension, the drug can be dispersed in the solvent phase using conventional techniques used in colloid chemistry. Depending on a variety of factors, e.g., the nature of the drug, those having ordinary skill in the art can select the solvent to form the solvent phase of the suspension, as well as the quantity of the drug to be dispersed in the solvent phase. The suspension can be mixed with a polymer solution and the mixture can be applied on the stent as described above. Alternatively, the drug suspension can be applied on the stent without being mixed with the polymer solution.

The drug-polymer layer can be applied directly onto at least a part of the stent surface to serve as a reservoir for at least one active agent or a drug, which is incorporated into the reservoir layer. The optional primer layer can be applied between the stent and the reservoir to improve the adhesion of the drug-polymer layer to the stent. The optional topcoat layer can be applied over at least a portion of the reservoir layer and serves as a rate limiting membrane which helps to control the rate of release of the drug. In one embodiment, the topcoat layer can be essentially free from any active agents or drugs. In another embodiment, besides the active agent or drug contained in the reservoir layer, the topcoat can incorporate an additional active agent or drug, for example, by having the additional drug or active agent conjugated to the polymer forming the topcoat layer. If a topcoat layer is used, the optional finishing coat layer can be applied over at least a portion of the topcoat layer for improving the biocompatibility of the coating.

The process of the release of the drug from a coating having both topcoat and finishing coat layers includes at least three steps. First, the drug is absorbed by the polymer of the topcoat layer on the drug-polymer layer/topcoat layer interface. Next, the drug diffuses through the topcoat layer using empty spaces between the macromolecules of the topcoat layer polymer as pathways for migration. Next, the drug arrives to the topcoat layer/finishing layer interface. Finally, the drug diffuses through the finishing coat layer in a similar fashion, arrives to the outer surface of the finishing coat layer, and desorbs from the outer surface. At this point, the drug is released into the blood stream. Consequently, a combination of the topcoat and finishing coat layers, if used, can serve as a rate limiting barrier.

In one embodiment, any or all of the layers of the stent coating can be made of a polymer that is biologically beneficial and biologically degradable, erodable, absorbable, and/or resorbable. In another embodiment, the outermost layer of the coating can be limited to such a polymer.

To illustrate in more detail, in the stent coating having all four layers described above (i.e., the primer, the reservoir layer, the topcoat layer and the finishing coat layer), the outermost layer is the finishing coat layer, which is made of a polymer that is biologically beneficial and biologically degradable, erodable, absorbable, and/or resorbable. In this case, optionally, the remaining layers (i.e., the primer, the reservoir layer, the topcoat layer) can also be fabricated from a polymer that is biologically beneficial and biologically degradable; the polymer can be the same or different in each layer.

If the finishing coat layer is not used, the topcoat layer can become the outermost layer and is made of a polymer that is both biologically beneficial and biologically degradable. In this case, optionally, the remaining layers (i.e., the primer and the reservoir layer) can be also fabricated of a polymer that is both biologically beneficial and biologically degradable; and the polymer can be the same or different in each of the four layers.

If neither the finishing coat layer nor the topcoat layer is used, the stent coating can have only two layers, the optional primer and the reservoir. The reservoir in this case is the outermost layer of the stent coating and is made of a polymer that is both biologically beneficial and biologically degradable. Optionally, the primer can be also fabricated of a biologically degradable and biologically beneficial polymer, which can be the same or different in the reservoir and in the primer.

The biological degradation, erosion, absorption and/or resorption of a biologically degradable, erodable, absorbable and/or resorbable and biologically beneficial polymer are expected to cause at least three results. First, the rate of release of the drug will increase due to the gradual disappearance of the polymer that forms the reservoir or the topcoat layer, or both. By choosing an appropriate degradable polymer, the stent coating can be engineered to provide either fast or slow release of the drug, as desired. Those having ordinary skill in the art can determine whether a stent coating having slow or fast release is advisable for a particular drug. For example, fast release may be recommended for stent coatings loaded with antimigratory drugs, which often need to be released within 1 to 2 weeks. For antiproliferative drugs, slow release may be needed (up to 30 days release time).

Second, if an additional active agent or drug is conjugated to the polymer of the topcoat layer, that active agent or drug is expected to be released as the polymer of the topcoat layer disappears as a result of degradation, erosion, absorption and/or resorption, thus providing additional therapeutic benefit. This embodiment is described in more detailed later in this application.

Third, upon degradation of a biologically degradable, erodable, absorbable and/or resorbable polymer, which is at the same time biologically beneficial, the products of degradation of the polymer can serve as other additional active agents which, can be absorbed by the body of the patient bringing about additional medical and biological benefits.

Biologically degradable, erodable, absorbable and/or resorbable polymers that which are also biologically beneficial and that can be used for making any of the stent coating layers, include block copolymers. Examples of block copolymers include ABA block copolymers, AB block copolymers, or polymers that are not necessarily block copolymers, as defined below, but still comprise ABA or AB blocks. Both ABA and AB block copolymers contain a polymeric moiety A and a polymeric moiety B.

One way of describing the ABA block copolymers is by using the formula $[-A-A-A]_m-[B-B-B]_n-[A-A-A]_p-$, where each of "m," "n," and "p" is an integer greater than 0. The AB block-copolymers can be described by the formula $[-A-A-A]_m-[B-B-B-]_n$, where each of "m" and "n" is an integer greater than 0. The blocks of the ABA and AB block copolymers need not be linked on the ends, since the values of the integers determining the number of A and B blocks ensure that the individual blocks are usually long enough to be considered polymers in their own right. Accordingly, the ABA block copolymer can be named poly-A-block-co-poly-B-block-co-poly-A-block copolymer, and the AB block copolymer can be named poly-A-block-co-poly-B-block copolymer. Blocks "A" and "B," typically larger than three-block size, can be alternating or random. The values of "m" and "p" can be selected to have the block copolymer with the molecular weight of blocks A between about 300 and about 40,000 Daltons, such as between about 8,000 and about 30,000 Daltons, for example, about 15,000 Daltons. The values of "n" are selected to have the block copolymer with the molecular weight of blocks B between about 50,000 and about 250,000 Daltons, such as between about 80,000 and about 200,000 Daltons, for example, about 100,000 Daltons.

In the ABA and AB block copolymers, one polymeric moiety can provide the block copolymer with blood compatibility ("a biocompatible moiety") and the other polymeric moiety ("a structural moiety") can provide the block copolymer with mechanical and adhesive properties that the block copolymer needs for making the stent coatings. In one embodiment, moiety A is the biocompatible moiety and moiety B is the structural moiety. In another embodiment, moiety A is the structural moiety and moiety B is the biocompatible moiety. The biocompatible and the structural moieties are selected to make the ABA and AB block-copolymers biologically degradable. Examples of suitable biocompatible moieties include poly(alkylene glycols), for example, poly(ethylene glycol) (PEG), poly(ethylene oxide), poly(propylene glycol) (PPG), poly(tetramethylene glycol), poly(ethylene oxide-co-propylene oxide), poly(N-vinyl pyrrolidone), poly(acrylamide methyl propane sulfonic acid) and salts thereof (AMPS and salts thereof), poly(styrene sulfonate), sulfonated dextran, polyphosphazenes, poly(orthoesters), poly(tyrosine carbonate), hyaluronic acid, hyaluronic acid having a stearoyl or palmitoyl substitutent group, copolymers of PEG with hyaluronic acid or with hyaluronic acid-stearoyl, or with hyaluronic acid-palmitoyl, heparin, copolymers of PEG with heparin, a graft copolymer of poly(L-lysine) and PEG, or copolymers thereof. A molecular weight of a suitable biocompatible polymeric moiety can be below 40,000 Daltons to ensure the renal clearance of the compound, for example, between about 300 and about 40,000 Daltons, more narrowly, between about 8,000 and about 30,000 Daltons, for example, about 15,000 Daltons.

Examples of suitable structural moieties include poly(caprolactone) (PCL), poly(butylene terephthalate) (PBT), poly(ester amide), moieties containing butyl methacrylate fragments, moieties containing a lauryl group, poly(lactic acid)(PLA), poly(aspirin), and copolymers thereof. Molecular weight of the blocks comprising the structural moiety can be between about 20,000 and about 250,000 Daltons, more narrowly, between about 80,000 and about 200,000 Daltons, such as about 100,000 Daltons.

One example of the biodegradable ABA block copolymer is poly(ethylene glycol)-block-poly(caprolactone)-block-poly(ethylene glycol)(PEG-PCL-PEG). One possible structure of the PEG-PCL-PEG block copolymer is shown by formula (I):

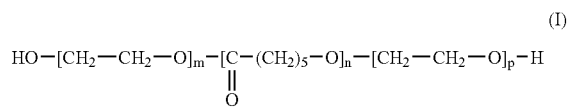

(I)

In the PEG-PCL-PEG block copolymers shown by formula (I), the PEG blocks constitute the biodegradable moiety, while the PCL block constitutes the structural moiety. If desired, the positions of the moieties can be switched to obtain a BAB block copolymer, poly(caprolactone)-block-poly(ethylene glycol)-block poly(caprolactone)(PCL-PEG-PCL). One possible structure of the PCL-PEG-PCL block copolymer is shown by formula (II):

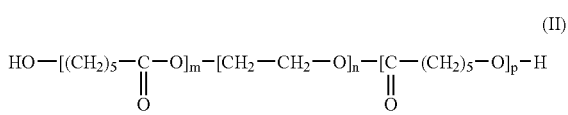

(II)

Block copolymers shown by formulae (I) and (II) can be synthesized by standard methods known to those having ordinary skill in the art, for example, by acid- or based-catalyzed copolycondensation of PEG with PCL. Another example of a PEG-containing polyester, suitable for making a stent and/or a stent coating in accordance with the present invention includes a block-copolymer of PEG with PBT, such as poly(ethylene glycol)-block-poly(butyleneterephthalate) (PEG-PBT), poly(ethylene glycol)-block-poly (butylene terephthalate)-block-poly(ethylene glycol) (PEG-PBT-PEG). PEG-PBT-PEG block-copolymer can be obtained, for example, by trans-esterification of dibutyleneterephthalate with PEG. Another example of the PEG-containing polyester, suitable for making a stent and/or a stent coating in accordance with the present invention includes a block-copolymer of PEG with PLA, such as poly(ethylene glycol)-block-poly(lactic acid)-block-poly(ethylene glycol) (PEG-PLA-PEG). In PEG-PLA-PEG, the molecular weight of the units derived from ethylene glycol can be between about 550 and about 30,000 Daltons, and the molecular weight of the units derived from lactic acid can be between about 20,000 and about 150,000 Daltons.

PEG-PBT and PEG-PBT-PEG block copolymers are known under a trade name POLYACTIVE and are available from IsoTis Corp. of Holland. In POLYACTIVE, the ratio between the units derived from ethylene glycol and the units derived from butylene terephthalate can be between about 0.67:1 and about 9:1. The molecular weight of the units derived from ethylene glycol can be between about 300 and about 4,000 Daltons, and the molecular weight of the units derived from butylene terephthalate can be between about 50,000 and about 250,000, for example, about 100,000 Daltons.

Alternatively, if desired, the positions of the moieties in the PEG-PBT-PEG and PEG-PLA-PEG block copolymers can be switched to obtain a BAB block copolymers, poly(butyleneterephthalate)-block-poly(ethylene glycol)-block-poly(butyleneterephthalate) (PBT-PEG-PBT) and poly(lactic acid)-block-poly(ethylene glycol)-block-poly(lactic acid) (PLA-PEG-PLA).

PEG-PCL-PEG, PCL-PEG-PCL, PEG-PBT, PEG-PBT-PEG, PBT-PEG-PBT, PEG-PLA-PEG and PLA-PEG-PLA block copolymers all contain fragments with ester bonds. Ester bonds are known to be water-labile bonds. When in contact with slightly alkaline blood, ester bonds are subject to catalyzed hydrolysis, thus ensuring biological degradability of the block copolymer. One product of degradation of every block polymer, belonging to the group PEG-PCL-PEG, PCL-PEG-PCL, PEG-PBT, PEG-PBT-PEG, PBT-PEG-PBT, PEG-PLA-PEG and PLA-PEG-PLA is expected to be PEG, which is highly biologically compatible. PEG also has an additional advantage of being biologically beneficial, reducing smooth muscle cells proliferation at the lesion site and thus capable of inhibiting restenosis.

In one embodiment, instead of, or in addition to, the ABA block copolymers and/or AB block copolymers described above, compounds other than ABA block copolymers and/or AB block copolymers can be used for making any layer of the stent coating, so long as these compounds are both biologically degradable and biologically beneficial. Examples of such compounds include polyaspirin and phosphoryl choline.

Any layer of the stent coating can contain any amount of the biodegradable ABA or AB block copolymers described above, or a blend of more than one such copolymers. If less than 100% of the layer is made of the biodegradable ABA or AB block copolymer(s), other, polymers can comprise the balance. Examples of the alternative polymers that can be used include polyacrylates, such as poly(butyl methacrylate), poly(ethyl methacrylate), and poly(ethyl methacrylate-co-butyl methacrylate), and fluorinated polymers and/or copolymers, such as poly(vinylidene fluoride) and poly (vinylidene fluoride-co-hexafluoro propene), poly(N-vinyl pyrrolidone), poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), co-poly(ether-esters), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, vinyl halide polymers and copolymers (such as polyvinyl chloride), polyvinyl ethers (such as polyvinyl methyl ether), polyvinylidene chloride, polyacrylonitrile, polyvinyl ketones, polyvinyl aromatics (such as polystyrene), polyvinyl esters (such as polyvinyl acetate), copolymers of vinyl monomers with each other and olefins, e.g., poly(ethylene-co-vinyl alcohol) (EVAL), ethylene-methyl methacrylate copolymers, acrylonitrile-styrene copolymers, ABS resins, and ethylene-vinyl acetate copolymers; polyamides (such as Nylon 66 and polycaprolactam), alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Representative examples of some solvents suitable for making the stent coatings include N,N-dimethylacetamide (DMAC), N,N-dimethylformamide (DMF), tethrahydrofuran (THF), cyclohexanone, xylene, toluene, acetone, i-propanol, methyl ethyl ketone, propylene glycol monomethyl ether, methyl butyl ketone, ethyl acetate, n-butyl acetate, and dioxane. Some solvent mixtures can be used, as well. Representative examples of the mixtures include:

(1) DMAC and methanol (e.g., a 50:50 by mass mixture);
(2) water, i-propanol, and DMAC (e.g., a 10:3:87 by mass mixture);
(3) i-propanol, and DMAC (e.g., 80:20, 50:50, or 20:80 by mass mixtures);
(4) acetone and cyclohexanone (e.g., 80:20, 50:50, or 20:80 by mass mixtures);
(5) acetone and xylene (e.g. a 50:50 by mass mixture);
(6) acetone, FLUX REMOVER AMS, and xylene (e.g., a 10:50:40 by mass mixture); and
(7) 1,1,2-trichloroethane and chloroform (e.g., an 80:20 by mass mixture).

FLUX REMOVER AMS is trade name of a solvent manufactured by Tech Spray, Inc. of Amarillo, Tex. comprising about 93.7% of a mixture of 3,3-dichloro-1,1,1,2,2-pentafluoropropane and 1,3-dichloro-1,1,2,2,3-pentafluoropropane, and the balance methanol, with trace amounts of nitromethane. Those having ordinary skill in the art will select a solvent or a mixture of solvents suitable for the particular polymer being dissolved.

The therapeutic substance that can be used in the reservoir layer can include any substance capable of exerting a therapeutic or prophylactic effect for a patient. The therapeutic substance may include small molecule substances, peptides, proteins, oligonucleotides, and the like. The therapeutic substance can be designed, for example, to inhibit the activity of vascular smooth muscle cells. It can be directed at inhibiting abnormal or inappropriate migration and/or proliferation of smooth muscle cells to inhibit restenosis.

Examples of therapeutic substances that can be used include antiproliferative substances such as actinomycin D, or derivatives and analogs thereof (manufactured by Sigma-Aldrich of Milwaukee, Wis., or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, anti-allergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as ANGIOMAX (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O-[2-(2-hydroxy)ethoxy]ethyl-rapamycin, and 40-O-tetrazole-rapamycin.

As mentioned above, the drug(s) can be conjugated to the polymer, to form a drug-polymer adduct. The drug-polymer adduct can be then used for making the reservoir and/or topcoat layer. In addition to the conjugated drug, the coating can be also impregnated with the drug. For example, the drug-polymer adduct can be dissolved in a suitable solvent, or a mixture of solvents, and the resulting solution of the drug-polymer adduct can be applied on the stent as described above.

The conjugated drug can include any substance capable of exerting a therapeutic or prophylactic effect in the practice of the present invention. Some examples of drugs that can be used for conjugation with the ABA block copolymer include paclitaxel, antisense agents (e.g., Rensten-NG), polyarginine (e.g., R7), rapamycin and structural derivatives or functional analogs thereof, such as EVEROLIMUS, 40-O-(3-hydroxy)propyl-rapamycin, 40-O-[2-(2-hydroxy)ethoxy]ethyl-rapamycin, and 40-O-tetrazole-rapamycin, and molecules that are sources of nitrogen oxide (NO) such as diazenium diolates.

One method of conjugating an additional drug to the ABA block copolymer is by utilizing the reactive functional groups of the copolymer. For instance, when the ABA block copolymer is PEG-PCL-PEG, the terminal hydroxyls of the PEG blocks can be used for carrying out the process of conjugating. Conjugating an additional drug to the ABA block copolymer can be illustrated by the process of binding diazenium diolate type nitric oxide donors to PEG-PCL-PEG.

Diazenium-diolate-type nitric oxide donors are adducts of nitric oxide with nucleophilic amines. Diazenium diolates, also known as "NONOates," are highly biologically compatible, and in slightly acidic media, they spontaneously release NO. One example of diazenium diolate that can be used is spermine diazenium diolate (SDD).

SDD, also known by its chemical name as 1,3-propanediamine, N-{4-[1-(3-aminopropyl)-2-hydroxy-2-nitrosohydrazino]butyl}-diazen-1-ium-1,2-diolate, is an aliphatic NONOate having the formula $NH_2$—$(CH_2)_3$—$N[N^+(O)$—$(N^+$—$OH)]$—$(CH_2)_4$—$NH$—$(CH_2)_3$—$NH_2$ and is available from Molecular Probes, Inc. of Eugene, Oreg. Alternatively, other diazenium-diolate-type NO donors can be used. Some examples of the alternative diazenium-diolate-type NO donors that can be conjugated to the PEG blocks of PEG-PCL-PEG include 1-{N-methyl-N-[6-(N-methylammonio)hexyl]amino}diazen-1-ium-1,2-diolate having the formula $CH_3$—$N^+H_2$—$(CH_2)_6$—$N(CH_3)$—$N^+(O^-)$=$N$—$O^-$ (MAHMA-NO), and Z-1-[N-(2aminoethyl)-N-(2-ammonioethyl)amino]diazen-1-ium-1,2-diolate having the formula $O$—$N^+[N(CH_2CH_2NH_2)CH_2CH_2N^+H_3]$=$N$—$O^-$ (DETA-NO). MAHMA-NO and DETA-NO can be obtained from Cayman Chemical Co. of Ann Arbor, Mich.

In order to carry out conjugation of SDD to a PEG-PCL-PEG block copolymer, the PEG block of the copolymer can be preliminarily derivatized by tosylation (treatment with tosyl chloride), or alternatively by tresylation (by reacting with tresyl chloride). Tosyl chloride is a derivative of toluene, para-toluenesulfonyl chloride, having the formula $CH_3$—$C_6H_4$—$SO_2Cl$ (TsCl). The process of PEG-PCL-PEG derivatization can be conducted outside the stent or directly on the stent. The processes of tosylation or tresylation include an attack on the terminal hydroxyl of the PEG block and can be illustrated by reactions (III) and (IV), respectively:

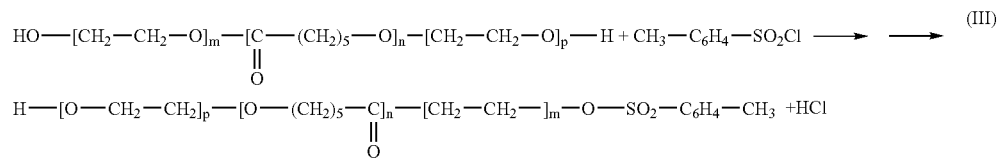

Alternatively, tresyl chloride (2,2,2-trifluoroethane-sulphonyl chloride) can be used to derivatrize PEG-PCL-PEG, according to reaction scheme (IV) and tresyl group is attached to the PEG-PCL-PEG backbone via hydroxy group:

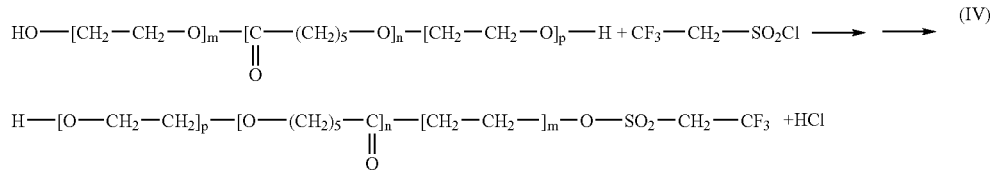

Next, tosylated or tresylated PEG-PCL-PEG can be modified by conjugating SDD. Due to the presence of two primary and one secondary amino groups, SDD is readily conjugated to the tosylated or tresylated PEG-PCL-PEG via alkylation of the amino groups. One possible process of conjugating can be shown for tosylated PEG-PCL-PEG as reaction (V):

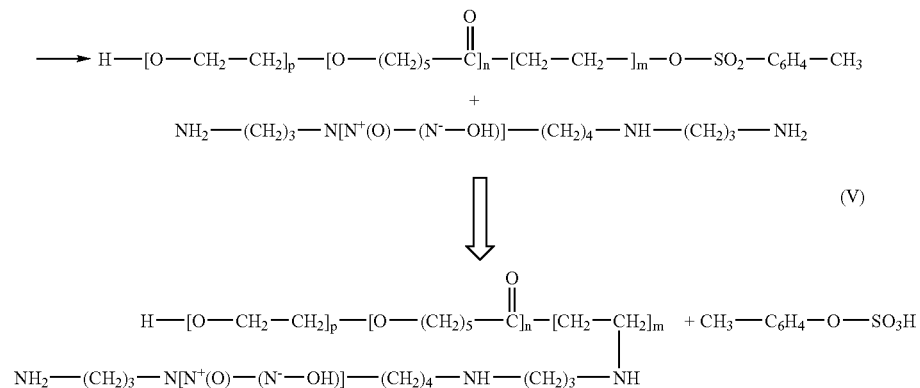

One or both PEG blocks of PEG-PCL-PEG can be modified with SDD according to the process described by reactions (III–V). Those having ordinary skill in the art can determine under which conditions the two-step process of conjugating SDD to PEG-PCL-PEG described by reactions (III–V) can be carried out. The resulting polymeric adduct can be described schematically as Dz-PEG-PCL-PEG (one PEG block is modified) or Dz-PEG-PCL-PEG-Dz (two PEG blocks are modified), where Dz is a fragment derived from SDD.

The coatings and methods of the present invention have been described with reference to a stent, such as a balloon expandable or self-expandable stent. The use of the coating is not limited to stents, however, and the coating can be used with a variety of other medical devices. Examples of the implantable medical device that can be used in conjunction with the embodiments of this invention include stent-grafts, grafts (e.g., aortic grafts), artificial heart valves, cerebrospinal fluid shunts, pacemaker electrodes, axius coronary shunts and endocardial leads (e.g., FINELINE and ENDOTAK, available from Guidant Corporation). The underlying structure of the device can be of virtually any design. The device can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention.

"MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

3. EXAMPLES

The following examples are provided to further illustrate embodiments of the present invention.

Example 1

A first composition can be prepared by mixing the following components:

(a) between about 1.0 mass % and about 15 mass %, for example, about 2.0 mass % poly(caprolactone) (PCL); and (b) the balance, DMAC solvent.

The first composition can be applied onto the surface of a bare 18 mm PENTA stent (available from Guidant Corporation) by spraying and dried to form a primer layer. A spray coater can be used having a 0.014 fan nozzle maintained at about 60° C. with a feed pressure of about 0.2 atm (about 3 psi) and an atomization pressure of about 1.3 atm (about 20 psi). About 70 μg of the wet coating can be applied. The primer can be baked at about 60° C. for about 2 hours, yielding a dry primer layer.

A second composition can be prepared by mixing the following components:

(a) between about 1.0 mass % and about 15 mass %, for example, about 2.0 mass % PEG-PCL-PEG, where the molecular weight of each PEG block can be about 10,000 Daltons, and the molecular weight of the PCL block can be about 70,000 Daltons;

(b) between about 0.05 mass % and about 2.0 mass %, for example, about 1.0 mass % paclitaxel; and (c) the balance, DMAC solvent.

The second composition can contain about 300 μg PEG-PCL-PEG and about 200 μg paclitaxel. The second composition can be applied onto the dried primer layer to form the reservoir layer, using the same spraying technique and equipment used for applying the primer layer, followed by drying, e.g., by baking as described above.

A third composition can be prepared by mixing the following components:

(a) between about 1.0 mass % and about 15 mass %, for example, about 2.0 mass % PEG-PCL-PEG;

(b) the balance, the DMAC solvent.

The third composition can be applied onto the dried reservoir layer to form a topcoat layer, using the same spraying technique and equipment used for applying the primer layer and the reservoir layer. About 200 μg of the wet coating can be applied, followed by drying, e.g., by baking as described above.

Example 2

The primer layer can be applied on a stent as described in Example 1.

A composition can be prepared by mixing the following components:

(a) between about 1.0 mass % and about 15 mass %, for example, about 2.0 mass % PEG-PCL-PEG;

(b) between about 1.0 mass % and about 15 mass %, for example, about 2.0 mass % PCL;

(c) between about 0.05 mass % and about 2.0 mass %, for example, about 1.0 mass % paclitaxel; and (c) the balance, DMAC solvent.

The composition can contain about 200 μg PEG-PCL-PEG, about 100 μg PCL, and about 200 μg paclitaxel. The composition can be applied onto the dried primer layer to form the reservoir layer, using the same spraying technique and equipment used for applying the primer layer, followed by drying, e.g., by baking as described above.

Example 3

The stent can be coated as described in Example 1, but instead of the topcoat layer that comprises PEG-PCL-PEG, the topcoat layer can be made of a Dz-PEG-PCL-PEG-Dz adduct.

Example 4

The stent can be coated as described in Example 1. A composition can be prepared by mixing the following components:

(a) between about 1.0 mass % and about 15 mass %, for example, about 2.0 mass % polyaspirin;

(b) between about 1.0 mass % and about 15 mass %, for example, about 2.0 mass % EVEROLIMUS; and (c) the balance, DMAC solvent.

The composition can contain about 150 μg polyaspirin, and about 100 μg EVEROLIMUS. The composition can be applied onto the dried topcoat layer to form the finishing coat layer, using the same spraying technique and equipment used for applying the primer layer, followed by drying, e.g., by baking as described above.

Example 5

The stent can be coated as described in Example 1, but instead of a reservoir layer that comprises paclitaxel, the reservoir layer can include EVEROLIMUS.

Example 6

A first composition can be prepared by mixing the following components:

(a) between about 1.0 mass % and about 15 mass %, for example, about 2.0 mass % PEG-PBT; and (b) the balance, a solvent blend comprising 1,1,2-trichloroethane and chloroform in a mass ratio between about 4:1.

The brand of PEG-PBT that can be used can have about 45 molar % PBT units and about 55 molar % PEG units. The molecular weight of the PEG units can be about 300 Daltons, and the molecular weight of the PBT blocks can be about 100,000 Daltons. The first composition can be applied onto the surface of a bare 18 mm PENTA stent to form a primer layer as described in Example 1. The primer can contain about 70 μg PEG-PBT.

After the primer layer has been formed, a reservoir layer comprising three sub-layers can be formed according to the following procedure. A second composition can be prepared by mixing the following components:

(a) between about 1.0 mass % and about 15 mass %, for example, about 2.0 mass % poly(L-arginine) R7; and (b) the balance, a solvent blend containing methanol and water in a mass ratio of about 3:1.

The second composition can be applied over the primer layer using techniques described above, and dried, e.g., by baking, to form a first reservoir sub-layer.

A third composition can be prepared by mixing the following components:

(a) between about 1.0 mass % and about 15 mass %, for example, about 2.0 mass % hyaluronic acid; and (b) the balance, a solvent blend containing ethanol and water in a mass ratio of about 3:1.

The third composition can be applied over the first reservoir sub-layer using techniques described above, and dried, e.g., by baking, to form a second reservoir sub-layer.

A fourth composition can be prepared by mixing the following components:

(a) between about 1.0 mass % and about 15 mass %, for example, about 3.0 mass % PEG-PBT; and (b) the balance, a solvent blend of 1,1,2-trichloroethane and chloroform described above.

The brand of PEG-PBT that can be used can have about 30 molar % PBT units and about 70 molar % PEG units. The molecular weight of the PEG blocks can be about 1,000 Daltons, and the molecular weight of the PBT blocks can be about 100,000 Daltons. The fourth composition can be applied over the second reservoir sub-layer using techniques described above, and dried, e.g., by baking to complete formation of the reservoir layer by forming a third reservoir sub-layer. The overall reservoir layer can contain about 300 μg R7, about 200 μg hyaluronic acid, and about 300 μg PEG-PBT.

A fifth composition can be prepared by mixing the following components:

(a) between about 1.0 mass % and about 15 mass %, for example, about 2.0 mass % PEG-PBT having about 20 molar % PBT units and about 80 molar % PEG units (The molecular weight of the PEG units can be about 4,000 Daltons);

(b) between about 1.0 mass % and about 15 mass %, for example, about 2.0 mass % an adduct of the same brand of PEG-PBT with hyaluronic acid; and (c) the balance the blend of 1,1,2-tricloroethane and chloroform described above.

The PEG-PBT-hyaluronic acid adduct can be synthesized by esterification of PEG-PBT with hyaluronic acid with a mass ratio between PEG-PBT and hyaluronic acid of about 2:1. Those having ordinary skill in the art can determine the conditions under which the esterification can be carried out.

The fifth composition can be applied onto the dried reservoir layer to form the topcoat layer, using the same spraying and drying techniques as described above. The topcoat layer can contain about 200 μg PEG-PBT, and about 100 μg hyaluronic acid.

Example 7

A first composition can be prepared by mixing the following components:

(a) between about 1.0 mass % and about 15 mass %, for example, about 2.0 mass % of a silk-elastin protein block copolymer; and (b) the balance, DMAC solvent.

Silk-elastin protein block copolymers combine repeating blocks of amino acids providing the copolymer with the mechanical strength characterizing silk and the flexibility characterizing elastin. Silk-elastin block copolymer can be obtained from Protein Polymer Technologies, Inc. of San Diego, Calif. The first composition can be applied onto the surface of a bare 18 mm PENTA stent to form a primer layer as described in Example 1. The primer can contain about 70 μg silk-elastin.

After the primer layer has been formed, a reservoir layer comprising two sub-layers can be formed according to the following procedure. A second composition can be prepared by mixing the following components:

(a) between about 1.0 mass % and about 15 mass %, for example, about 2.0 mass % poly(L-arginine) R7; and (b) the balance, a solvent blend containing methanol and water in a mass ratio of about 3:1.

The second composition can be applied over the primer layer using techniques described above, and dried, e.g., by baking, to form a first reservoir sub-layer.

A third composition can be prepared by mixing the following components:

(a) between about 1.0 mass % and about 15 mass %, for example, about 2.0 mass % hyaluronic acid;

(b) between about 1.0 mass % and about 15 mass %, for example, about 2.0 mass % silk-elastin; and (c) the balance, a solvent blend containing methanol and water in a mass ratio of about 3:1.

The third composition can be applied over the first reservoir sub-layer using techniques described above, and dried, e.g., by baking, to complete formation of the reservoir layer by forming a second reservoir sub-layer. The overall reservoir layer can contain about 100 μg R7, about 100 μg hyaluronic acid, and about 100 μg silk-elastin.

A fourth composition can be prepared by mixing the following components:

(a) between about 1.0 mass % and about 15 mass %, for example, about 2.0 mass % silk-elastin; and (b) the balance, a solvent blend containing methanol and water in a mass ratio of about 3:1.

The fourth composition can be applied over the reservoir layer using techniques described above, and dried, e.g., by baking, to form an to form an intermediate layer. The intermediate layer can contain about 50 μg silk-elastin.

A fifth composition can be prepared by mixing the following components:

(a) between about 1.0 mass % and about 15 mass %, for example, about 2.0 mass % PEG-PBT having about 20 molar % PBT units and about 80 molar % PEG units (The molecular weight of the PEG units can be about 4,000 Daltons);

(b) between about 1.0 mass % and about 15 mass %, for example, about 2.0 mass % PEG-PBT having about 45 molar % PBT units and about 55 molar % PEG units. The molecular weight of the PEG units can be about 300 Daltons; and (c) the balance, the blend of 1,1,2-trichloroethane and chloroform described above.

The fifth composition can be applied onto the dried reservoir layer to form a topcoat layer using the same spraying and drying techniques, as described above. The topcoat layer can then be annealed by heating to about 80° C. for about 30 minutes and then to about 50° C. for about 1 hour. The topcoat layer can contain about 100 μg of each kind of PEG-PBT.

Example 8

A stent can be coated with a primer layer as described in Example 6. A first composition can be prepared, comprising:

(a) between about 1.0 mass % and about 15 mass %, for example, about 2.0 mass % PEG-PBT having about 45 molar % PBT units and about 55 molar % PEG units (The molecular weight of the PEG units can be about 300 Daltons);

(b) between about 1.0 mass % and about 15 mass %, for example, about 2.0 mass % EVEROLIMUS;

(c) the balance, the blend of 1,1,2-trichloroethane and chloroform described above.

The composition can contain about 100 μg PEG-PBT, and about 100 μg EVEROLIMUS. The composition can be applied onto the dried primer layer to form the reservoir layer using the same spraying technique and equipment used for applying the primer layer, followed by drying, e.g., by baking, as described above.

A second composition can be prepared by mixing the following components:

(a) between about 1.0 mass % and about 15 mass %, for example, about 2.0 mass % PEG-PBT; and (b) the balance, the blend of 1,1,2-trichloroethane and chloroform described above.

The same kind of PEG-PBT as the one used for making the reservoir layer can be used. The second composition can be applied over the reservoir layer using techniques described above, and dried, e.g., by baking, to form an intermediate layer. The intermediate layer can contain about 70 μg PEG-PBT. The reservoir layer/the intermediate layer sequence can be repeated 4 times to achieve a total EVEROLIMUS load of about 400 μg.

Following formation of the reservoir layer/intermediate layer system, the topcoat layer can be formed as described in Example 7.

Example 9

A stent can be coated with a primer layer as described in Example 6. A first composition can be prepared, comprising:

(a) between about 1.0 mass % and about 15 mass %, for example, about 2.0 mass % PEG-PBT having about 45 molar % PBT units and about 55 molar % PEG units (The molecular weight of the PEG units can be about 300 Daltons);

(b) between about 1.0 mass % and about 15 mass %, for example, about 2.0 mass % EVEROLIMUS;

(c) the balance, the blend of 1,1,2-trichloroethane and chloroform described above.

The composition can contain about 100 µg PEG-PBT, and about 100 µg EVEROLIMUS. The composition can be applied onto the dried primer layer to form a reservoir layer, using the same spraying technique and equipment used for applying the primer layer, followed by drying, e.g., by baking, as described above.

A second composition can be prepared, comprising:

(a) between about 1.0 mass % and about 15 mass %, for example, about 2.0 mass % PEG-PBT having about 45 molar % PBT units and about 55 molar % PEG units (The molecular weight of the PEG units can be about 300 Daltons);

(b) between about 1.0 mass % and about 15 mass %, for example, about 2.0 mass % polyaspirin; and (c) the balance, the blend of 1,1,2-tricloroethane and chloroform described above.

The second composition can be applied over the reservoir layer using techniques described above, and dried, e.g., by baking, to form an intermediate layer. The intermediate layer can contain about 50 µg PEG-PBT and about 50 µg polyaspirin. The reservoir layer/intermediate layer sequence can be repeated 4 times to achieve a total EVEROLIMUS load of about 400 µg and a total polyaspirin load of about 200 µg.

A third composition can be prepared by mixing the following components:

(a) between about 1.0 mass % and about 15 mass %, for example, about 2.0 mass % PEG-PBT having about 45 molar % PBT units and about 55 molar % PEG units (The molecular weight of the PEG units can be about 300 Daltons);

(b) between about 1.0 mass % and about 15 mass %, for example, about 2.0 mass % polyaspirin; and (c) the balance, the blend of 1,1,2-trichloroethane and chloroform described above.

The third composition can be applied onto the dried reservoir layer/intermediate layer system to form a topcoat layer using the same spraying and drying techniques as described above. The topcoat layer can then be annealed by being heated to about 80° C. for about 30 minutes and then to about 50° C. for about 1 hour. The topcoat layer can contain about 100 µg PEG-PBT and about 200 µg polyaspirin.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A medical article comprising an implantable substrate having a coating, the coating including an ABA or an AB block copolymer, the block copolymer having A and B blocks and an active agent conjugated to the block copolymer, wherein one of the blocks comprises a biological moiety and the other block comprises a structural moiety that provides the block copolymer with structural functionality, wherein the structural moiety comprises poly(butylene terephthalate), poly(ester amide), poly(lactic acid), or copolymers thereof, and wherein the active agent conjugated to the block copolymer is diazenium diolate.

2. The medical article of claim 1, wherein the medical article is a stent.

3. The medical article of claim 1, wherein block A comprises the biological moiety, and block B comprises the structural moiety.

4. The medical article of claim 1, wherein block B comprises the biological moiety, and block A comprises the structural moiety.

5. The medical article of claim 1, wherein the biological moiety is selected from a group consisting of poly(alkylene glycols), poly(ethylene oxide), poly(ethylene oxide-co-propylene oxide), poly(N-vinyl pyrrolidone), poly(acrylamide methyl propane sulfonic acid) and salts thereof, sulfonated dextran, polyphosphazenes, poly(orthoesters), poly(tyrosine carbonate), hyaluronic acid, hyaluronic acid having a stearoyl or palmitoyl substitutent group, poly(ethylene glycol)-hyaluronic acid, poly(ethylene glycol)-hyaluronic acid-stearoyl, poly(ethylene glycol)-hyaluronic acid-palmitoyl, heparin, poly(ethylene glycol)-heparin, and copolymers thereof.

6. The medical article of claim 5, wherein the poly (alkylene glycol) is selected from a group consisting of poly(ethylene glycol), poly(propylene glycol), poly(tetramethylene glycol), a graft copolymer of poly(L-lysine) and poly(ethylene glycol), and copolymers thereof.

7. The medical article of claim 1, wherein the block copolymer is selected from a group consisting of poly (ethylene-glycol)-block-poly(butyleneterephthalate)-block-poly(ethylene-glycol), poly(butyleneterephthalate)-block-poly(ethylene-glycol)-block poly(butyleneterephthalate), poly(ethylene-glycol)-block-poly(butyleneterephthalate), poly(ethylene-glycol)-block-poly(lactic acid)-block-poly(ethylene-glycol), poly(lactic acid)-block-poly(ethylene-glycol)-block-poly(lactic acid) and blends thereof.

8. The medical article of claim 1, additionally comprising a first biologically active agent incorporated into the coating.

9. The medical article of claim 1, additionally comprising an active agent conjugated to the block copolymer.

10. The medical article of claim 1, wherein the coating further comprises phosphoryl choline or polyaspirin.

11. A method for fabricating a medical article, the method including applying a coating on at least a portion of an implantable substrate, the coating including an ABA or an AB block copolymer, the block copolymer having A and B blocks and an active agent conjugated to the block copolymer, wherein one of the blocks comprises a biological moiety and the other block comprises a structural moiety that provides the block copolymer with structural functionality, wherein the structural moiety comprises poly(butylene terephthalate), poly(ester amide), poly(lactic acid), or copolymers thereof, and wherein the active agent conjugated to the block copolymer is diazenium diolate.

12. The method of claim 11, wherein the medical article is a stent.

13. The method of claim 11, wherein block A comprises the biological moiety, and block B comprises the structural moiety.

14. The method of claim 11, wherein block B comprises the biological moiety, and block A comprises the structural moiety.

15. The method of claim 11, wherein the biological moiety is selected from a group consisting of poly(alkylene glycols), poly(ethylene oxide), poly(ethylene oxide-co-propylene oxide), poly(N-vinyl pyrrolidone), poly(acrylamide methyl propane sulfonic acid) and salts thereof, sulfonated dextran, polyphosphazenes, poly(orthoesters), poly(tyrosine carbonate), hyaluronic acid, hyaluronic acid having a stearoyl or palmitoyl substitutent group, poly(ethylene glycol)-hyaluronic acid, poly(ethylene glycol)-hyaluronic acid-stearoyl, poly(ethylene glycol)-hyaluronic acid-palmitoyl, heparin, poly(ethylene glycol)-heparin, and copolymers thereof.

16. The method of claim 11, wherein the poly(alkylene glycol) is selected from a group consisting of poly(ethylene glycol), poly(propylene glycol), poly(tetramethylene glycol), a graft copolymer of poly(L-lysine) and poly(ethylene glycol), and copolymers thereof.

17. The method of claim 11, wherein the block copolymer is selected from a group consisting of poly(ethylene-glycol)-block-poly(butyleneterephthalate)-block-poly(ethylene-glycol), poly(butyleneterephthalate)-block-poly(ethylene-glycol)-block poly(butyleneterephthalate), poly(ethylene-glycol)-block-poly(butyleneterephthalate), poly(ethylene-glycol)-block-poly(lactic acid)-block-poly(ethylene-glycol), poly(lactic acid)-block-poly(ethylene-glycol)-block-poly(lactic acid) and blends thereof.

18. The method of claim 11, additionally comprising a first biologically active agent incorporated into the coating.

19. The method of claim 11, additionally comprising an active agent conjugated to the block copolymer.

* * * * *